United States Patent [19]
Jorgenson et al.

[11] Patent Number: 5,131,998
[45] Date of Patent: Jul. 21, 1992

[54] TWO-DIMENSIONAL HIGH-PERFORMANCE LIQUID CHROMATOGRAPHY/CAPILLARY ELECTROPHORESIS

[75] Inventors: James W. Jorgenson, Chapel Hill, N.C.; Michelle M. Bushey, San Antonio, Tex.

[73] Assignee: The University of North Carolina at Chapel Hill, Chapel Hill, N.C.

[21] Appl. No.: 612,662

[22] Filed: Nov. 13, 1990

[51] Int. Cl.$^5$ .................. B01D 61/42; C25D 13/00
[52] U.S. Cl. .................. 204/299 R; 210/656; 210/198.2
[58] Field of Search .............. 204/299 R, 180.1, 183.3

[56] References Cited

U.S. PATENT DOCUMENTS 4,676,897 6/1987 Kuze et al. .................. 204/183.3
4,708,782 11/1987 Andresen et al. .................. 204/180.1

OTHER PUBLICATIONS

Janssen et al., J. Chrom., 470, 171–183 (1989).
R. Nielsen et al., J. Chrom., 480, 393–401 (1989).
Yamamoto et al., 480, 277–283 (1989) Chromatography.
M. Bushey and J. Jorgenson, Anal. Chem. 62, 161–167 (1990).
J. Davis and J. Giddings, Anal. Chem. 57, 2168–2177 (1985).
J. Davis and J. Giddings, Anal. Chem 57, 2178–2182 (1985).
J. Giddings, J. High Resolut. Chromatogr. Commun. 10, 319–323 (1987).
J. Green and J. Jorgenson, J. Chromatogr. 352, 337–343 (1986).
P. Grossman et al., Anal. Chem. 61, 1186–1194 (1989).
P. Janssen et al., J. Chromatogr. 470, 171–183 (1989).
R. Nielsen et al., J. Chromatogr. 480, 393–401 (1989).
H. Yamamoto et al., J. Chromatogr. 480, 277–283 (1989).

Primary Examiner—John Niebling
Assistant Examiner—Caroline Koestner
Attorney, Agent, or Firm—Bell, Seltzer, Park & Gibson

[57] ABSTRACT

Disclosed is a two-dimensional separation system, comprising a liquid chromatography column having an outlet port; a capillary electrophoresis capillary having an inlet end and an outlet end; buffer supply means for supplying buffer to the capillary; and valve means connecting the capillary inlet end to the chromatography column outlet port and to the buffer supply means, the valve means switchable between a first configuration providing fluid to the capillary inlet end from the buffer supply means and a second configuration providing fluid to the capillary inlet end from the chromatography column. Methods of carrying out two-dimensional separations employing the system are also disclosed.

16 Claims, 6 Drawing Sheets

TWO-DIMENSIONAL HIGH-PERFORMANCE LIQUID CHROMATOGRAPHY/CAPILLARY ELECTROPHORESIS

This invention was made with government support under Grant No. CHE-8912926 from the National Science Foundation. The government may have certain rights to this invention.

FIELD OF THE INVENTION

This invention relates to 2-dimensional separation method and apparatus involving liquid chromatography followed by capillary electrophoresis.

BACKGROUND OF THE INVENTION

Because substantially greater peak capacity and resolution can be obtained by 2-dimensional separation systems, a variety of 2-dimensional and coupled separation mechanisms have been developed. The coupling of liquid chromatography and gas chromatography to mass spectrometry, MS-MS, LC with electrochemical detection, coupled column techniques and other such systems can produce a wealth of information on complex samples. In the article "Comprehensive 2-Dimensional HPLC" (Bushey, M. and Jorgenson, J., Anal. Chem. 1990, 62, 161-167) a method was presented which coupled ion exchange chromatography and size exclusion chromatography in a manner such that all of the effluent from the first column was reanalyzed on the second column without the use of stopped flow methods.

Many samples need to undergo more than one separation mechanism to reduce peak overlaps (Davis, J. and Giddings, J., Anal. Chem. 1985, 57, 2168-2177; Davis, J. and Giddings, J., Anal. Chem. 1985, 57, 2178-2182). For two techniques to be satisfactorily coupled, however, several criteria need to be addressed. Most importantly, the two techniques should be as orthogonal to each other as possible (i.e., the two techniques should base their respective separations on as different sample properties as possible). The orthogonality aspect creates an interesting problem in the design of 2-D separation systems; the more orthogonal two separation mechanisms are, the more dissimilar they will be in operation, and the more dissimilar the two systems are in operation, the more difficult it will probably be to couple the two systems.

Reversed phase chromatography (RP HPLC) and capillary zone electrophoresis (CZE) are presumably highly orthogonal separation methods. Based on this, they are good candidates for pairing in a 2-D system. Several groups have already recognized this and have used CZE to analyze collected RP HPLC fractions of enzymatic digests of proteins and to compare the tryptic digest fingerprints of RP HPLC and CZE (Puma, P. et al., poster M-P-126 presented at HPCE '89, Boston, Mass., Apr. 10-12, 1989; Nielsen, R. et al., J. Chromatogr. 1989, 480, 393-40; Grossman, P. et al., Anal. Chem 1989, 61, 1186-1194). The unsurprising result in these cases is that CZE is found to be able to resolve some peptides that co-elute on RP HPLC. Although no one has actually reexamined collected CZE fractions by RP HPLC, by careful examination of RP HPLC and CZE tryptic digest maps of human growth hormone, Nielsen and coworkers (J. Chromatogr. 1989, 480, 393-40) have shown that the opposite is true also; that RP HPLC is capable of resolving peptides that co-migrate in CZE. This is not a surprising result, especially considering those species with zero net charge that migrate at the velocity of the electroosmotic flow and are thus unresolved by CZE. Pairing electrophoretic separations with chromatography has also been done using isotachophoresis as a purity check for RP HPLC analysis of peptides (Janssen, P. et al., J. Chromatogr. 1989, 470, 171-183).

Only one other group that we are aware of has attempted to automate the coupling of HPLC with CZE. That attempt coupled a Sephadex G-50 size exclusion column as the first dimension separation to isotachophoresis as the second dimension separation. Second dimension analysis times, however, were very long at 18 minutes each, stopped flow methods were used on the first column during the second dimension separation, and 3-D "chromatoelectropherograms" were not presented. The system was used to analyze a sample containing bovine serum albumin, myoglobin and tyrosine (Yamamoto, H. et al., J. Chromatogr. 1989, 480, 277-283). There is, accordingly, a clear need for new 2-D analysis systems

SUMMARY OF THE INVENTION

The present invention is based on our work with the automated coupling of reverse phase microbore chromatography and capillary zone electrophoresis.

A first aspect of the present invention is a two-dimensional separation system, comprising a liquid chromatography column having an outlet port; a capillary electrophoresis capillary having an inlet end and an outlet end; buffer supply means for supplying buffer to the capillary; and valve means connecting the capillary inlet end to the chromatography column outlet port and to the buffer supply means, the valve means switchable between a first configuration providing fluid to the capillary inlet end from the buffer supply means and a second configuration providing fluid to the capillary inlet end from the chromatography column.

Preferably, the system further comprises a waste line connected to the valve means, wherein the valve means in the first configuration conducts effluent from the chromatography column to the waste line.

A sample storage loop may be connected to the valve means and a waste line connected to the valve means, with the valve means switchable between a run configuration and an inject configuration; and with the valve means in the run configuration simultaneously (a) conducting effluent from the chromatography column through the storage loop and to the waste line, and (b) conducting effluent from the buffer supply means directly to the capillary inlet end; and with the valve means in the inject configuration simultaneously (a) conducting effluent from the chromatography column directly to the waste line, and (b) conducting effluent from the buffer supply means through the storage loop and to the capillary, whereby a sample of effluent from the chromatography column in the storage loop is flushed into the capillary by the buffer supply means.

Shunt means may be connected between the valve means and the capillary for directing excess effluent away from the capillary inlet. A pump is preferably included to provide a means for supplying a continuous stream of input solution to the liquid chromatography column. And a detector may be operably associated with the capillary electrophoresis capillary for detecting molecules in the capillary. A power supply may be operably connected to both the capillary inlet end and the capillary outlet end and configured for providing a potential therebetween so that the inlet end serves as an anode and the outlet end serves as a cathode, and charged molecules in the capillary are carried from the inlet end to the outlet end by electromigration.

Another aspect of the present invention is a two-dimensional separation system, comprising: a liquid chromatography column having an outlet port; a capillary electrophoresis capillary having an inlet end and an outlet end; valve means connecting the capillary inlet end to the chromatography column outlet port, the valve means switchable between a first configuration not providing fluid to the capillary from the chromatography column and a second configuration providing fluid to the capillary from the chromatography column; control means operably associated with the valve means for switching the valve means between the first configuration and the second configuration; and a power supply operably connected to both the capillary inlet end and the capillary outlet end configured for providing a potential therebetween so that the inlet end serves as an anode, the outlet end serves as a cathode, and charged molecules in the capillary are carried from the inlet end to the outlet end by electromigration; with the power supply operably associated with the control means; and wherein the control means reduces the potential between the capillary inlet end and the capillary outlet end when the valve means is in the second position by an amount sufficient to hinder the electromigration of charged molecules therein. In a preferred embodiment the control means reduces the potential between between the anode and the cathode at a predetermined time prior to switching the valve means from the first configuration to the second configuration, wherein the predetermined time is at least equal to the slew time required to reduce the potential between the capillary inlet end and the capillary outlet end by an amount sufficient to hinder the electromigration of charged molecules therein. The control means may restore the potential between the capillary inlet end and the capillary outlet end when the valve means is switched from the second configuration to the first configuration. The system may further comprise a detector operably associated with the capillary for detecting molecules in the capillary, with the control means operably associated with the detector for collecting data therefrom, and wherein the control means interrupts data collection from the detector upon reducing the potential between between the capillary inlet end and the capillary outlet end. A buffer supply means may be connected to the valve means for supplying buffer to the capillary; and wherein the valve means in the first configuration provides fluid to the capillary from the buffer supply means. In a preferred embodiment a sample storage loop is connected to the valve means and a waste line is connected to the valve means, and the valve means is switchable between a run configuration and an inject configuration; with the valve means in the run configuration simultaneously (a) conducting effluent from the chromatography column through the storage loop and to the waste line, and (b) conducting effluent from the buffer supply means directly to the capillary; and with the valve means in the inject configuration simultaneously (a) conducting effluent from the chromatography column directly to the waste line, and (b) conducting effluent from the buffer supply means through the storage loop and to the capillary, whereby a sample of effluent from the chromatography column in the storage loop is flushed into the capillary by the buffer supply means.

Another aspect of the present invention is a subassembly useful in constructing a two-dimensional separation system which includes a first separation system, a second capillary electrophoresis separation system comprised of a capillary having an inlet end and an outlet end, and a power supply operably connected to both the capillary inlet end and the capillary outlet end and configured for providing a potential therebetween so that the inlet end serves as an anode, the outlet end serves as a cathode, and charged molecules in the capillary are carried from the inlet end to the outlet end by electromigration; the subassembly comprising: valve means for connecting to the capillary inlet end to the first separation system, the valve means switchable between a first configuration not providing fluid to the capillary from the first separation system and a second configuration providing fluid to the capillary from the first separation system; and control means operably associated with the valve means for switching the valve means between the first configuration and the second configuration; wherein the control means includes means for reducing the potential between between the capillary inlet end and the capillary outlet end when the valve means is in the second position by an amount sufficient to hinder the electromigration of charged molecules therein.

Also provided is a two-dimensional separation method, comprising: providing a first stream of aqueous solution containing molecules to be detected from a first separation system; providing a second stream of aqueous buffer solution; providing a capillary electrophoresis capillary having an inlet end and an outlet end; maintaining a potential between the capillary inlet end and the capillary outlet end so that the inlet end serves as an anode, the outlet end serves as a cathode, and charged molecules in the capillary are carried from the inlet end to the outlet end by electromigration; and continuously passing aqueous solution across the capillary inlet end by alternately providing the first stream and the second stream of aqueous solution to the capillary inlet end.

A fourth aspect of the invention is a twodimensional separation method, comprising: providing a liquid chromatography column as a first dimension; providing a capillary electrophoresis capillary as a second dimension; continuously passing a solution containing a mixture of molecules to be detected through the column to provide an effluent therefrom, the effluent containing the molecules to be detected in a concentration which varies over time and provides at least one first dimension peak therein; and sampling the effluent in the second dimension at a frequency sufficient to sample each first dimension peak at least twice in the second dimension.

BRIEF DESCRIPTION OF THE DRAWINGS

FIG. 8 shows all plots from data set in FIG. 7.

DETAILED DESCRIPTION OF THE PREFERRED EMBODIMENTS

Figure 1:
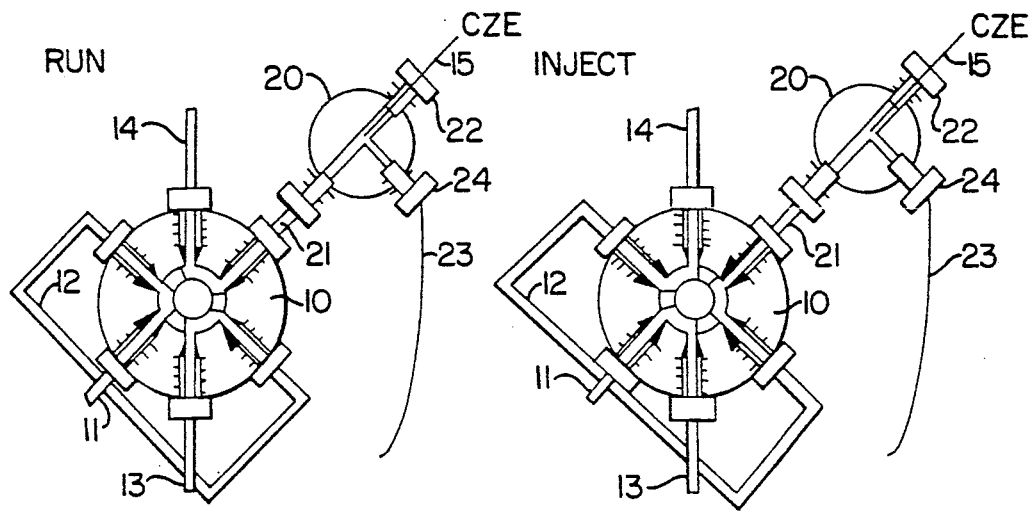
FIG. 1 shows two configurations of a six-port valve used in carrying out the present invention.

Instrumentation. The coupling of a liquid chromatography column with capillary electrophoresis is accomplished through the use of a 6-port valve assembly 10 as shown in FIG. 1. The valve assembly operates in a first "run" configuration and a second "inject" configuration, with both being illustrated in FIG. 1. In the "run" position, effluent from the LC column in line 11 fills the sample storage loop 12 and from there goes to the waste line 13 while the effluent from second pump serving as a buffer supply means in line 14 continuously forces fresh buffer coaxially past the grounded (anode) inlet end of the capillary zone electrophoresis (CZE) capillary 15. In the inject position, the liquid chromatography column effluent from line 11 goes directly to waste line 13 while buffer input from line 14 forward flushes the contents of storage loop 12 past the grounded end of the CZE capillary 15 for electromigration injection. At the end of the injection time the valve is returned to the "run" position. Timing and control of the valve movements are described in the subsection "control unit".

A Valco Instruments Co., Inc. (Houston, Tex.) low dead volume tee 20 is connected to the valve via a short section of stainless steel tubing 21. This tubing had an inner diameter of 0.007" and a length of 5 cm. The fused silica CE capillary 15 extends into the tee and terminates near the center of the tee. The capillary is held in place by a Valco fused silica adapter 22. A second piece of fused silica capillary 23 with an i.d. of 325 $\mu$m is similarly connected to the third tee port via adapter 24 to carry away waste solvent. This part can also provide a means to collect fractions eluting from the RP column.

Figure 2:
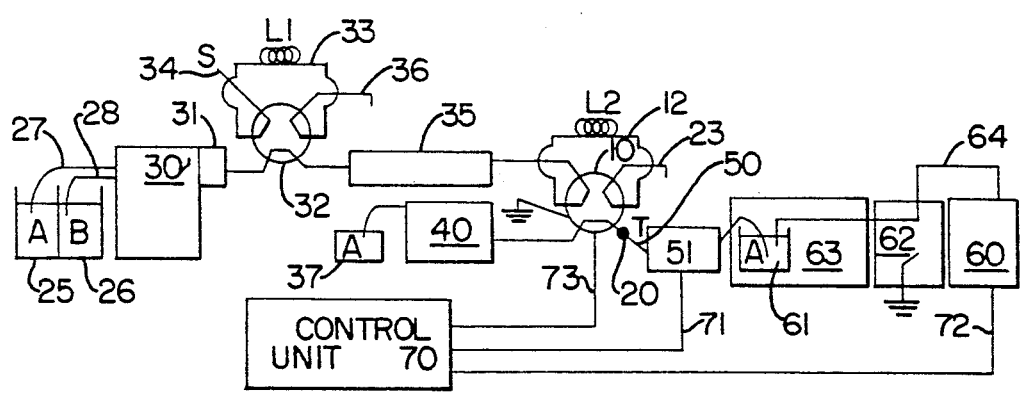
FIG. 2 provides a schematic diagram of the 2-D LC-CZE instrumentation of the present invention. A and B are Buffer A and acetonitrile, respectively.

FIG. 2 is a schematic diagram of an apparatus of the present invention. A Brownlee Microgradient Syringe Pump 30 (Santa Clara, Calif.) is fitted with a Brownlee 5 $\mu$L mixer column 31. Associated with mixer column 31 is a manually operated 6-port valve 32 with 1/16 inch fittings and a standard port diameter of 0.016 inch (valve material is Nitronic 60) and may be purchased from Valco Instruments Co., Inc. (Houston, Tex.). The loop 33 provided on the valve 32 is a Valco 50 $\mu$L loop. A 100 $\mu$L Hamilton Syringe fitted with a 2-inch, 22 g needle purchased from Alltech Associates (Waukegan, Ill.) 34 is provided in association with valve 32. A Brownlee Aquapore RP-300 reversed phase column 35, 250 mm × 1.0 which may be purchased through Rainin Instrument Co., Inc.(Woburn, Mass.) is connected to valve 32.

A Waters Association (Milford, Mass.) model 6000A piston pump 40 is included as the buffer supply means. Valve assembly 10 is a 6-port electrically actuated valve similar to valve 32 except the valve material for is Hastelloy C. The sample storage loop 12 is a Valco 10 $\mu$L loop (19 cm length, 0.26 mm i.d.). All connecting tubing, unless otherwise noted, is 0.007 inch inner diameter and 1/16 inch fittings are used.

The entire valve is held at electrical ground and functions as the anode for the CZE system. An alligator clip placed on the stainless steel valve body and connected to ground ensures that the connection to ground is maintained.

The fused silica capillaries 50 used were 41 $\mu$m i.d. and 150 $\mu$m o.d., and also 50 $\mu$m i.d. and 150 $\mu$m o.d.. Each was cut to a total length of 38 cm. Currently preferred are fused silica capillaries which are 15 $\mu$m i.d. and 150 $\mu$m o.d., and which are cut to a length of 26 cm. Fused silica capillary may be purchased from Polymicro Technologies (Phoenix, Ariz.). No capillary surface pretreatments or coatings are used.

A short section of the polyimide coating is burned off of the fused silica capillary to create a detection window. The distance from the center of this window to the grounded (injection) end of the capillary measures 6.5 cm. The fused silica capillary was mounted in the low dead volume tee 20 as described in FIG. 1.

The detector 51 used in this work has been described elsewhere (See Green, J. S.; Jorgenson, J. W. J. Chromatogr. 1986, 352, 337–343). It is a variable wavelength fluorescence detector. An excitation wavelength of 365 nm is isolated with a double monochrometer. The slit width is 10 nm. A 470 nm cut on emission filter is used.

A +/− 30 kV dc power supply 60 with the remote voltage programming option may be obtained from Spellman High Voltage Electronic Corp. (Plainview, N.Y.), and is used in the negative voltage mode. The direction of migration for all analytes is from the positive to the negative electrode. The negative end of the CZE capillary 50 terminates in a vial containing the same buffer as that being pumped by pump 40 which is the same as Buffer A on 35. The buffer in this vial is levelled to prevent hydrodynamic flow in the capillary. A grounding box 62 and interlock box 63 of the type known to one skilled in the art are used for operator safety. A microammeter ($\mu$A) (not shown) is placed between the high voltage electrode and CZE buffer vial inside the interlock box to monitor the current.

The first dimension separation can be run independently of the CZE system by moving line 11 to port 14 in FIG. 1 and replacing the CZE system with a short piece of fused silica, held in valve 10 by a Valco fused silica adapter such as 22. Valve 10 is moved to the "run" position for this type of operation. This procedure allows for coupling of the microbore RP column to the capillary fluorescence detector 51. Effluent from 35 flows through valve 10 directly to the piece of fused silica 50 tubing mounted in the detector 51 and empties to waste on the opposite side of the detector.

The second dimension (CZE) separation can be run independently of the LC system by replacing line 11 in FIG. 1 with a Valco syringe port. A 50 $\mu$L Hamilton syringe is then used to fill the 10 $\mu$L loop for a single injection on the CZE portion of the system. The valve 10 can then be actuated manually or through computer control.

Control Unit. The control unit 70 may consist of an IBM ® or compatible personal computer, and fitted with a Labmaster multifunction input/output interface board which may be purchased from Scientific Solutions (Solon, Ohio). The control unit records data, controls the valve switching of valve 10 shown in FIGS. 1 and 2, and controls the high voltage power supply 60. The interface board consists of a 16-bit analog-to-digital converter (ADC) which acquires data from the output of the fluorescence detector photometer 51 via connection 71, a 100 microFarad capacitor is placed across the ADC input. The interface board of control unit 70 also contains a 12-bit digital-to-analog converter which controls the level of high voltage applied during the analysis through the remote voltage programming option of power supply 60 via connection 72; a programmable parallel port (Intel 8255) which controls position of valve 10 via connection 73 and the on/off control of the power supply 60 via connection 72; a programmable timer (Advanced MicroSystem 9513) is used for timed data acquisition, timed valve movements and timed voltage changes. Data acquisition rates depend upon the particular application.

Computer Programs. Hardware and LC-CZE instrumentation are under the control of software routines running in the control unit. Software routines running in the control unit may allow for user entered parameters such as CZE injection and run voltages, CZE injection time lengths and run times, number of CZE runs, and data acquisition rate. The injection time and run time variables determine the frequency of movements of valve 10. Bookkeeping data with regards to other run conditions may also be entered. At the completion of the analysis, another portion of the software routines processes the data. The data may be converted to a compatible form for use with plotting software, such as Surfer version 4.0 (Golden Graphics Software, Golden, Colo.). Several options may be available for data processing. For example, using the Golden Graphics Software, (a) the data can be presented as a 3-D chromatoelectropherogram viewed from any angle or height, where the x axis represents the migration time on the CZE system, the y axis represents the chromatogram retention time and the z axis is detector response. Any combination of X,Y or Z lines may be plotted; (b) Golden Graphics Software also allows for contour maps of the 3-D data; entire chromatoelectropherograms or portions thereof may be plotted in either of these two forms. It should be recognized that software routines may be written which allow for other forms of data presentation such as: (a) individual electropherograms can be displayed; (b) any number of electropherograms can be summed together and displayed; the resulting display of the summation of all electropherograms is a simulation of the electropherogram of the total original sample; (c) a chromatogram "slice" of the 3-D plot can be displayed; (d) the width of this "slice" may be varied by summing individual chromatogram "slices", summing all slices produces a simulation of the chromatogram of the total original sample, smaller widths are the simulated chromatograms for a particular electrophoretic mobility range. Furthermore, additional methods of display may be employed such as on screen grey scale images of the 2-D data.

Figure 3:
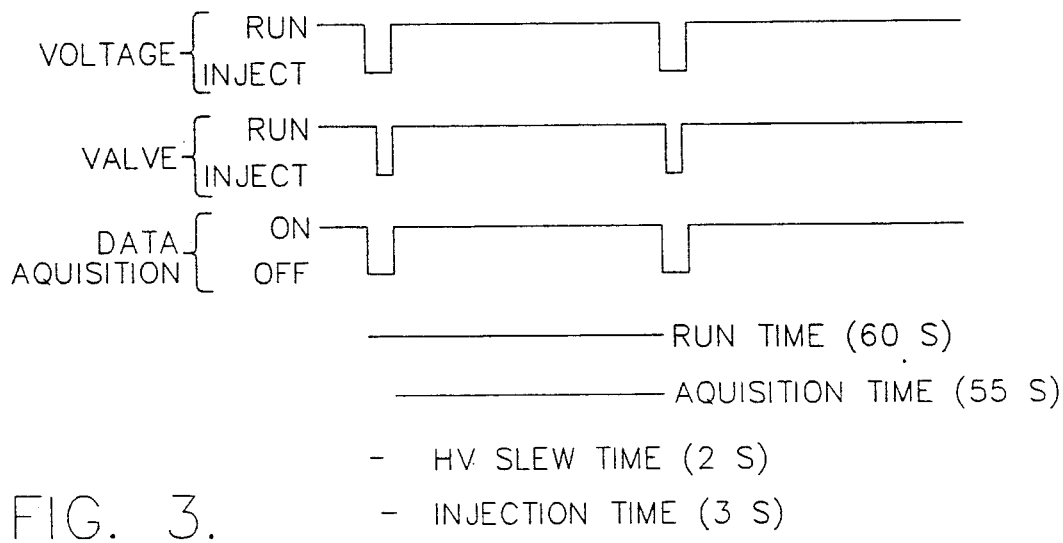
FIG. 3 graphically illustrates a computer program timing diagram drawn to scale. The diagram assumes a 1 minute "run" time, 3 second injection time and 2 second high voltage power supply slew time; actual data acquisition time is equal to run time minus HV slew time and injection time.

There are several considerations in the timing aspects of this system's operation. An example timing diagram is illustrated in FIG. 3. In this diagram, a user entered value of one minute is assumed for the length of the CZE run time. A user entered value of 3 seconds is assumed for the length of the CZE injection time. Because the shortest injection time possible is limited by the switching time of valve 10, the voltage of power supply 60 must be lowered by control unit 70 for these injections. Otherwise, band broadening due to excessively large injection slugs is the result. Another consideration is the time it takes the voltage of power supply 60 to drop from the high voltage value to ground. In the present example it takes approximately 2 seconds for the voltage of power supply 60 to drop from −30 kV to 0 kV. A faster drop can be facilitated by operation of grounding box 62 but this has a tendency to interfere with control unit 70 and over the course of a several hour run would cause unnecessary wear on the solenoid in grounding box 62. Therefore, prior to each movement of valve 10 to the inject position, there is a 2 second interval during which no data is collected and the voltage of power supply 60 is allowed to drop from the run voltage to the injection voltage. This 2 second high voltage slew time interval is constant regardless of any other run parameters. At the end of the 2 second interval valve 10 is turned to the inject position and the electromigration injection is begun and continues for the length of time entered by the user. No data is collected during the injection period. At the end of the injection time valve 10 is returned to the "run" position, voltage is returned to the run voltage value and data acquisition is resumed in that order. This entire sequence of 2 second interval, injection time and data collection time takes place during the user entered "CZE run time". Therefore, CZE data acquisition times are actually shorter than the user specified time, and the time allowed for the RP column to fill the loop on 41 is equal to the user specified run time minus the injection time. This also means 35 always underfills 42 by about 0.5 μL each injection cycle. However, since 14 overflushes the loop during a CZE injection, this small amount of underfilling is unimportant.

While a preferred embodiment has been described above, those skilled in the art will appreciate that capillary electrophoresis apparatus other than capillary zone electrophoresis can be employed in practicing the present invention, including capillary gel electrophoresis, capillary isotachophoresis, micellar electrokinetic capillary chromatography, and capillary isoelectric focusing.

It will also be apparent that any type of liquid chromatography column may be used in practicing the present invention, including reverse phase chromatography columns, size exclusion chromatography columns, ion exchange chromatography columns, adsorption chromatography columns, and affinity chromatography columns. Particularly prefered are reverse phase chromatography columns and size exclusion chromatography columns.

Where appropriate, aspects of the present invention may be carried out with a first separation system other than a liquid chromatography system, such as by employing capillary electrophoresis or gel electrophoresis as the first separation system.

The present invention is useful for separating complex molecules from one another when provided in a solution containing a plurality of different molecules (i.e., a crude solution). Complex molecules which may be separated with the present invention include proteins, glycoproteins, peptides, amino acids, and polynucleic acids. The molecules may be charged molecules or may be associated with a charged group, such as in micellar electrokinetic capillary chromatography.

Any suitable detector and detection means may be used to carry out the present invention. For example, detection of molecules may be carried out by ultraviolet absorption, fluorescence, electrochemical detection, mass spectrometry, refractive index detection, and chemiluminescence.

When fluorescence is used as the detection means the molecules to be detected may be labelled with a fluorescent group. Fluorescent molecules which may be used in connection with this invention are exemplified by fluorescein and fluorescein derivatives, dansyl chloride (5-dimethylaminonaphthylene-1-sulfonyl chloride) and analogs thereof, coumarin and coumarin analogs, and fluorescamine. Numerous other suitable fluorescent molecules are available.

EXPERIMENTAL

This example is set forth to demonstrate and explain in greater detail the operation of an apparatus as described above. It is provided for illustrative purposes only, and is not to be taken as limiting of the invention.

Samples and Reagents. Each analysis is performed using a 0.012 M potassium phosphate buffer at pH 6.9 which is prepared daily from a single 0.2 M stock solution to minimize day-to-day changes in the reverse phase chromatography and electrophoresis. This solution is referred to as Buffer A. Buffer A is used on the RP column as well as in the CZE system. Deionized water is further purified with a Barnstead Nanopure System (Boston, Mass.). All solutions were filtered with 0.22 μm pore size MAGNA Nylon 66 membrane filters from Micron Separations, purchased from Fisher Scientific (Raleigh, N.C.). Reagent grade acetonitrile is purchased from Fisher Scientific. The following were purchased from Sigma Chemical Co. (St. Louis, Mo.): chicken egg albumin (ovalbumin), fluorescamine (fluram), riboflavin, bovine pancreatic trypsin, angiotensin I, met-leu-phe, methionine enkephalinamide and leucine enkephalin.

Digest Conditions. 0.1 gm of ovalbumin is dissolved in 10 mL of Buffer A. One drop of brilliant yellow solution is then added to help monitor the pH change when the pH is adjusted to 8.0 with NH4OH. The solution is heated in a boiling water bath for 6 minutes. After cooling, 2.0 mg of trypsin is added to the solution and the digest solution is allowed to react for 4 hours at 37° C. The digest is stored at 4 degrees Centigrade until needed. This procedure is based on previous work in both our lab (Jorgenson, J. et al., *HRC&CC J. High Resolut. Chromatogr. Chromatogr. Commun.* 1981, 4, 230–231) and other labs (Canfield, R. et al., *J. Biol. Chem.* 1963, 238, 2684–2690).

Tagging Conditions for Digest. 0.5 mg of fluorescamine is dissolved in 50 μL of acetonitrile. The digested protein peptide sample is adjusted to pH 9.0 with KOH. 100 μL of the peptide solution is added to the 50 μL fluorescamine solution. 500 μL of Buffer A is added to this solution. The resulting solution is used as the injection sample. Samples were used within 5 minutes of tagging.

Tagging Conditions for Peptide Standards. 2.0 mg of met-leu-phe and angiotensin I were each added separately to 1 mL aliquots of Buffer A which had been adjusted to pH 9.0. 1.0 mg of methionine enkephalinamide and leucine enkephalin were each added separately to 1 mL of Buffer A at pH 9.00. 1.0 mg of fluorescamine is dissolved in 100 μL of acetonitrile. 20 μL of this solution is added to 40 μL of each of the four peptide standard solutions. 20 μL of each of the resulting four solutions were mixed together and 300 μL of Buffer A at pH 6.9 is added to the sample mixture. In addition, 20 μL of each of the four tagged peptide solutions were also added to 300 μL of Buffer A separately. These four separate samples were used on the CZE system for identification of the peptides by migration time.

Riboflavin solutions. 0.4 mg of riboflavin is dissolved in 20 μL of Buffer A. 20 μL of this solution is added to the following nine solutions: 80 μL of Buffer A; 70 μL Buffer A, 10 μL acetonitrile; 60 μL Buffer A, 20 μL acetonitrile; 50 μL Buffer A, 30 μL acetonitrile; 40 μL Buffer A, 40 μL acetonitrile; 30 μL Buffer A, 50 μL acetonitrile; 20 μL Buffer A, 60 μL acetonitrile; 10 μL Buffer A, 70 μL acetonitrile; 80 μL acetonitrile. The resulting solutions were each $10^{-5}$ M in riboflavin and used over a 180 minute run time to simulate injections from solutions that were 0%, 10%, 20%, 30%, 40%, 50%, 60%, 70% and 80% acetonitrile respectively.

System Preparation Each day fresh Buffer A is aspirated through the CZE capillary. −15 kV is then applied for 15 minutes. Prior to the start of the 2-D run, the sample is manually injected on the CZE capillary to verify that electrophoretic analysis will be completed during the specified run time, and to recheck the injection parameters such as voltage, time, and flow rate of pump 40. The CZE capillary is aspirated again with Buffer A before reconnection of the 2-D system and the start of the first column gradient. Due to limited memory in the control unit, the operation of the CZE portion of the system is not begun until a short time before the elution of the first peak from the RP column. This time is determined by prior operation of the RP column independent of the CZE system. Only relatively minor elution time variations from day-to-day have been observed on the RP column.

separation Conditions. Peptide standards: a 10 μL/min flow rate is used on column 35. The mobile phase is held isocratic in Buffer A for 10 minutes. The gradient is begun at 10 minutes and the mobile phase is changed from 0% to 25% acetonitrile from 10 to 100 minutes; from 100 to 200 minutes the mobile phase is changed from 25% to 50% acetonitrile; from 200 to 230 minutes the mobile phase is changed from 50% to 75% acetonitrile; from 230 to 290 minutes the mobile phase is changed from 75% to 90% acetonitrile. Due to limited memory in the control unit, the CZE injections were not begun until 204 minutes and continued until 264 minutes. 60 injections on the CZE system were made. One CZE injection is made every minute. The flow rate on pump 40 is 0.5 mL/min, the injection voltage is −2 kV, and valve 10 is held in the inject position for 5 seconds to ensure complete flushing of the 10 μL loop 12. The CZE run voltage is −19 kV. A 50 μm i.d. CZE capillary is used. The data collection rate is 5 pts/sec. Tryptic digest: a 10 μL/min flow rate is used on C1. The mobile phase is held isocratic in Buffer A for the first 10 minutes. A gradient from 0% acetonitrile to 30% acetonitrile ran from 10 minutes to 175 minutes. From 175 to 300 minutes the mobile phase is changed from 30% to 90% acetonitrile. CZE injections were begun at 95 minutes and continued until 275 minutes; 180 injections were made. One injection every minute is performed with a flow rate of 0.4 mL/min on pump 40. Valve 10 is held in the inject position for 3 seconds for each injection and the injection voltage is −3 kV. The CZE run voltage is −22 kV. A 10 μm i.d. CZE capillary is used. The data acquisition rate is 5 pts/sec. To investigate any changes in the electroosmotic flow in the CZE system, manual injections of riboflavin solutions were made approximately every 20 minutes on a 50 μm i.d. capillary. 180 valve rotations were performed; every 20th rotation the loop is filled with the appropriate riboflavin sample to simulate a gradient from 0% to 80% acetonitrile from 0 to 160 minutes. The flow rate on pump 40 is 0.4 mL/min. The injection voltage is −3 kV; the run voltage is −15 kV. Valve 10 is held in the inject position for 5 seconds. One CZE injection is made every minute. The data acquisition rate is 3 pts/sec.

Figure 4:
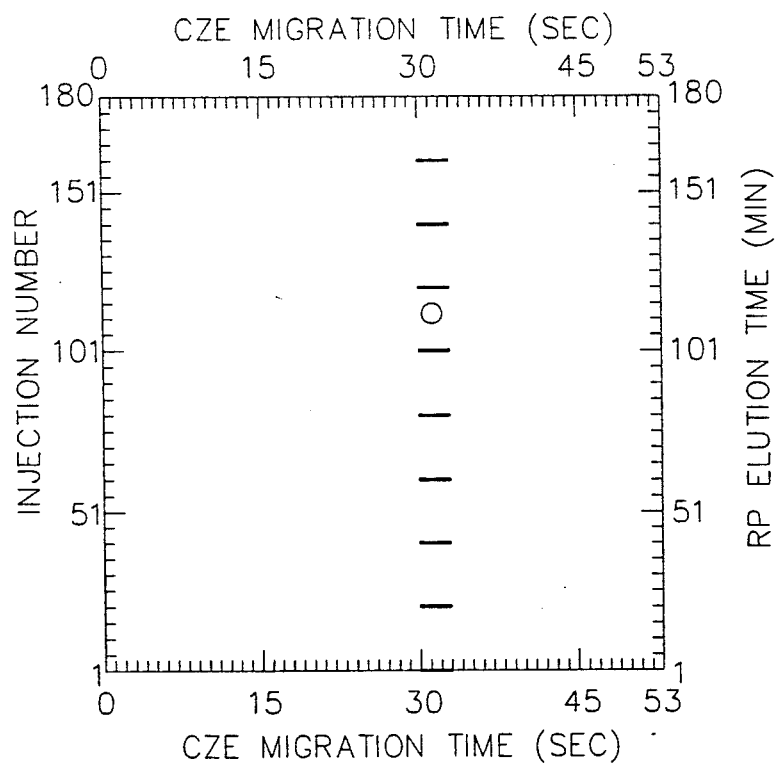
FIG. 4 shows a contour plot of riboflavin injections. Buffer A flowrate, 0.4 mL/min; injection voltage, −3 kV; injection time, 5 seconds; run voltage, −15 kV; run time, 1 minute; 1 riboflavin injection every 20 minutes, valve operated every minute; injections 1 through 180 plotted; samples simulate a gradient from 0% to 80% acetonitrile as described in the text; buffer A, 0.012 M potassium phosphate, pH 6.9; capillary: 50 $\mu$m i.d., 150 $\mu$m o.d., 6.5 cm to detector, 38 cm total length; data acquisition rate is 3 pts/sec.; every point is plotted.

RESULTS. FIG. 4 is a contour map of 9 injections of riboflavin on the CZE portion of the 2-D system. One injection was made approximately every 20 minutes from solutions made to simulate a gradient of 0% to 80% acetonitrile over a 160 minute time frame as described above. The RP column was removed and replaced with a syringe port for these injections. In between injections valve 10 was operated but no injections were made. The entire data acquisition time for each CZE run is shown to illustrate the magnitude of electroosmotic flow change with respect to the full run time. Tic marks on the CZE migration time axis represent 1 second each. Tic marks on the injection number axis represent 5 injections each. Table 1 lists the migration time (first statistical moment) for all 9 injections and their compositions as well as the standard deviation and RSD. The RSD of the first statistical moment for these peaks is 1.18%. This variability, as can be seen in Table I and examination of FIG. 4, is due more to a slight gradual increase in the electroosmotic flow rather than a more scattered type of variation from injection to injection. This means a single peak eluting from the LC column over the course of several CZE injections would be largely unaffected by this variability (if this type of variability is typical of all 2-D runs).

TABLE 1

CZE Migration Time as a Function of Sample Solvent Composition

| Percent Acetonitrile | First Moment, s |
|---|---|
| 0 | 32.0 |
| 10 | 32.1 |
| 20 | 31.8 |
| 30 | 31.6 |
| 40 | 31.3 |
| 50 | 31.2 |
| 60 | 31.2 |
| 70 | 31.2 |
| 80 | 31.2 |

Standard Deviation 0.372
Relative Std. Dev. 1.18%

Although the electroosmotic flow can change significantly from one day to another (which necessitates daily optimization of the CZE parameters prior to 2-D operation as stated in the EXPERIMENTAL section) no evidence has been seen indicating significant variation within the time period of one 2-D run.

Figure 5A:
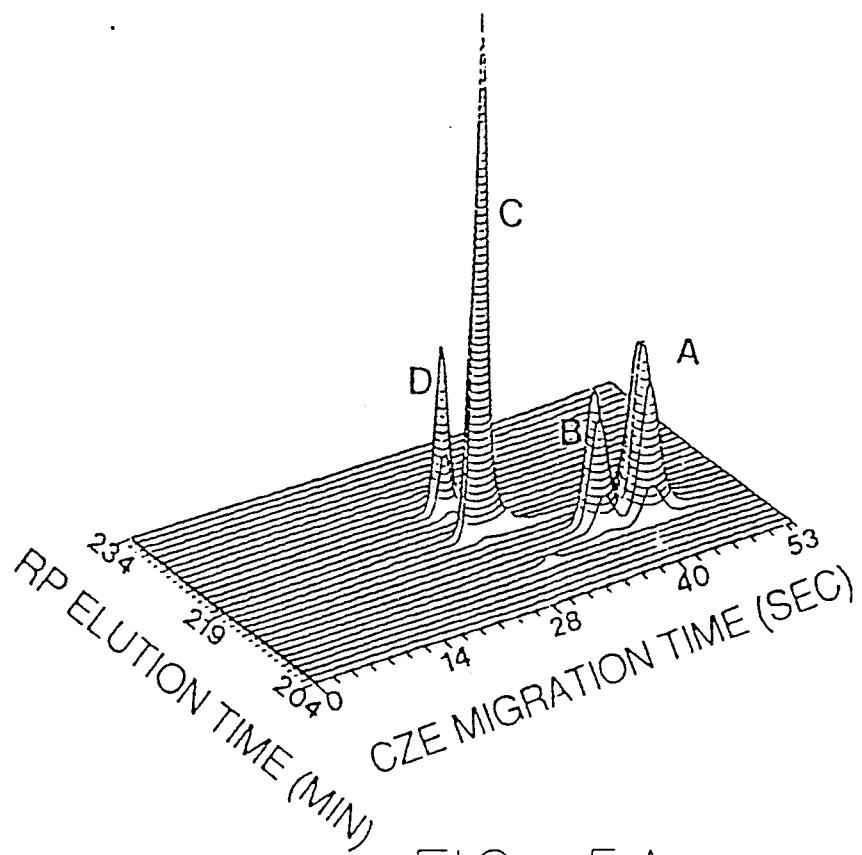
FIG. 5(a) shows a computer generated 3-D chromatoelectropherogram of fluorescamine labelled peptide standards. Peaks identified as follows: A, met-leu-phe; B, leucine enkephalin; C, angiotensin I; D, methionine enkephalinamide; P1 flowrate 10 $\mu$L/min.; gradient conditions described in EXPERIMENTAL section; Buffer A flowrate, 0.5 mL/min.; injection voltage −2 kV; injection time, 5 seconds; run voltage, −19 kV; run time, 1 minute; injections 1 through 30 plotted; data acquisition rate, 5 pts/sec.; every other point plotted; CZE capillary, 50 $\mu$m i.d., 150 $\mu$m o.d., 6.5 cm to detector, 38 cm total length.
Figure 5B:
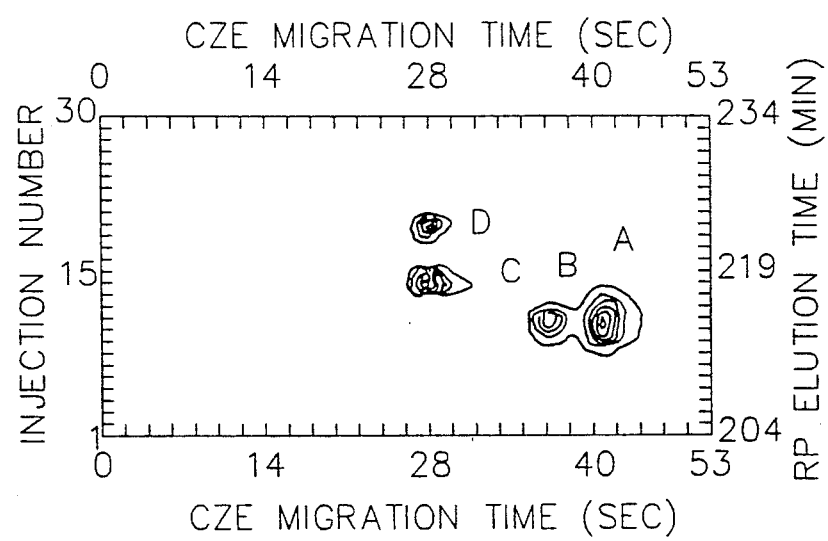
FIG. 5(b) shows a 15 contour plot of the same chromatoelectropherogram.

FIGS. 5a and 5b are computer generated plots of a chromatoelectropherogram of leucine enkephalin, met-leu-phe, angiotensin I and methionine enkephalinamide; all of which were labelled with fluorescamine. Run conditions are listed in the Brief Description of the Drawings. The symmetrical peak shapes are evidence that electroosmotic flow variation between neighboring runs on the CZE system is insignificant. A factor which may have contributed to the extremely steady electroosmotic flow is the continuous supply of fresh buffer at the CZE capillary anode. These plots nicely demonstrate the increased separating power of 2-D operation. Neither method, used alone, could separate all four analytes under these conditions, but in combination with each other, these four peptides are cleanly resolved.

Figure 6A:
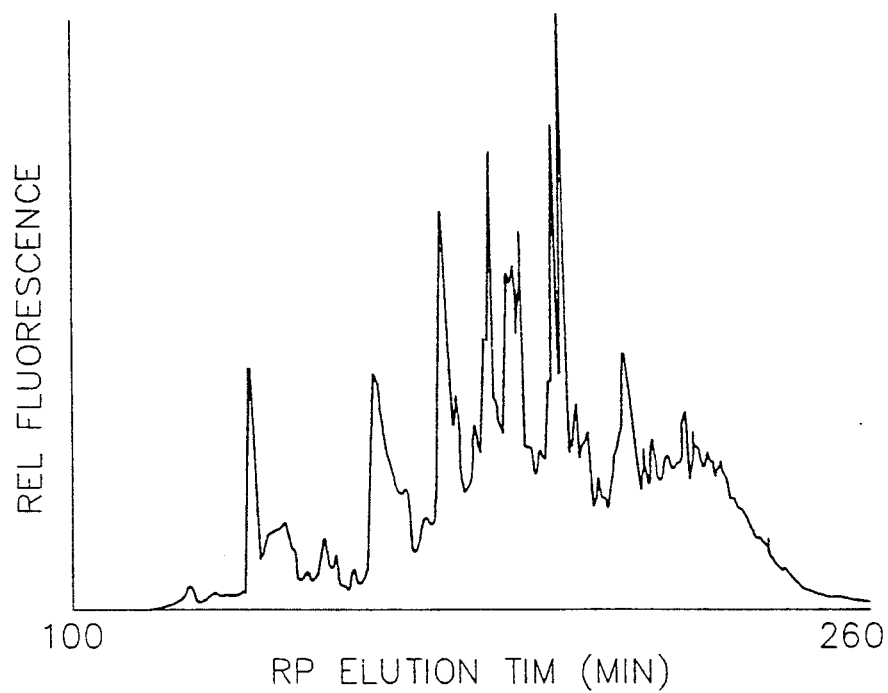
FIG. 6(a) shows a single dimension RP chromatogram of fluorescamine labelled tryptic digest of ovalbumin. Reverse phase column flow rate, 10 $\mu$L/min.; gradient: 0 to 10 min., isocratic in Buffer A; 10–175 minutes, 0% to 30% acetonitrile; 175 to 300 min., 30% to 90% acetonitrile; data acquisition rate is 0.5 pts/sec; X axis tic marks are at 1 min. intervals.

FIG. 6a is a single dimension chromatogram of a RP separation of the tryptic digest of ovalbumin, again labelled with fluorescamine. Although a slower gradient might effect a more complete separation, size of memory in the controller limits the total length of time during which the CZE portion of the system can operate at a sufficient data acquisition rate. There are two very small peaks that elute at approximately 23 minutes which is not in the time frame sampled by the CZE system. In any case, this is a complex sample which is clearly not completely resolved by use of the RP column alone. Tic marks on the x axis are at one minute intervals, indicating how this separation would have been "fractionated" for CZE runs had a full 2-D analysis been performed. Assuming an elution time range from 120 to 260 minutes and peaks 4 minutes wide at the base, this dimension has a peak capacity of approximately 35 under these gradient conditions (probably a conservative estimate).

Figure 6B:
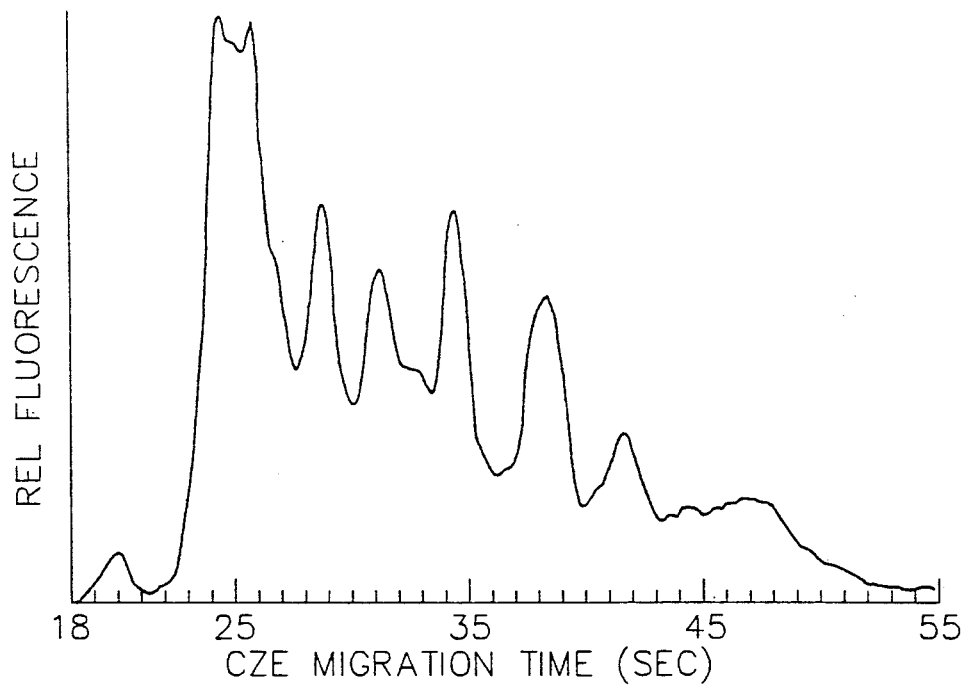
FIG. 6(b) shows a single dimension electropherogram of fluorescamine labelled tryptic digest ovalbumin. Buffer A flowrate, 0.4 mL/min, buffer A; injection voltage, −3 kV; injection time, 3 seconds; run voltage, −22 kV; run time, 1 min.; data acquisition rate is 6 pts/sec.; capillary, 41 $\mu$m i.d., 150 $\mu$m o.d., 6.5 cm to detector, 38 cm total length.

FIG. 6b is a single dimension electropherogram of the same fluorescamine labelled digest sample. This electropherogram was obtained as described above by replacing column 35 in FIG. 2 with a syringe port and a user entered value of one for the number of CZE injections. Assuming a migration time range of 18 to 55 seconds and 3 second wide peaks, this dimension has a peak capacity of approximately 12. Based upon these estimates for peak capacity in both dimensions, the 2-D operation of this system should have a peak capacity of at least 420. One aspect that should be noted in FIG. 6b is the mobility discrimination observed with electromigration injection. Late eluting peaks which have low mobilities are discriminated against in the injection. Smaller peaks later in the electropherogram are the result. A hydrodynamic injection method for use with 2-D operation, which should correct this problem, will be investigated in this lab. Both of these figures demonstrate the complexity of the sample and the inadequacy of either technique to fully resolve the sample when operated independently of each other.

Figure 7A:
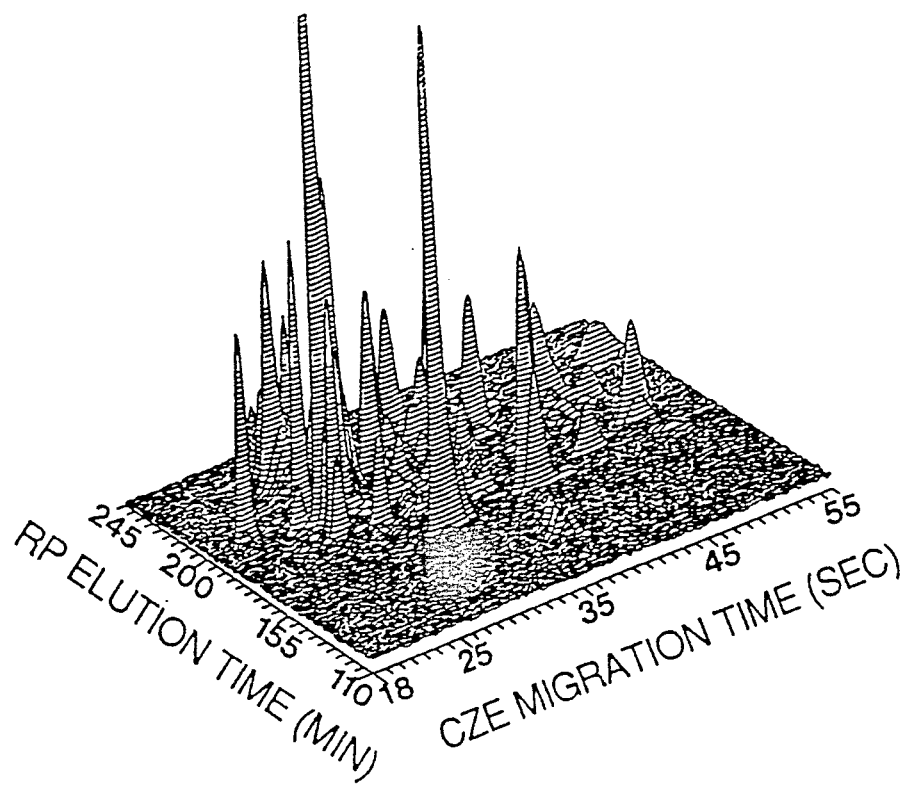
FIG. 7(a) shows a computer generated chromatoelectropherogram of fluorescamine labelled tryptic digest of ovalbumin. Same conditions as in FIG. 6 with the following exceptions: Data acquisition rate is 5 pts/sec.; all points from 18 to 55 seconds are plotted; injections 15 through 150 plotted.
Figure 7B:
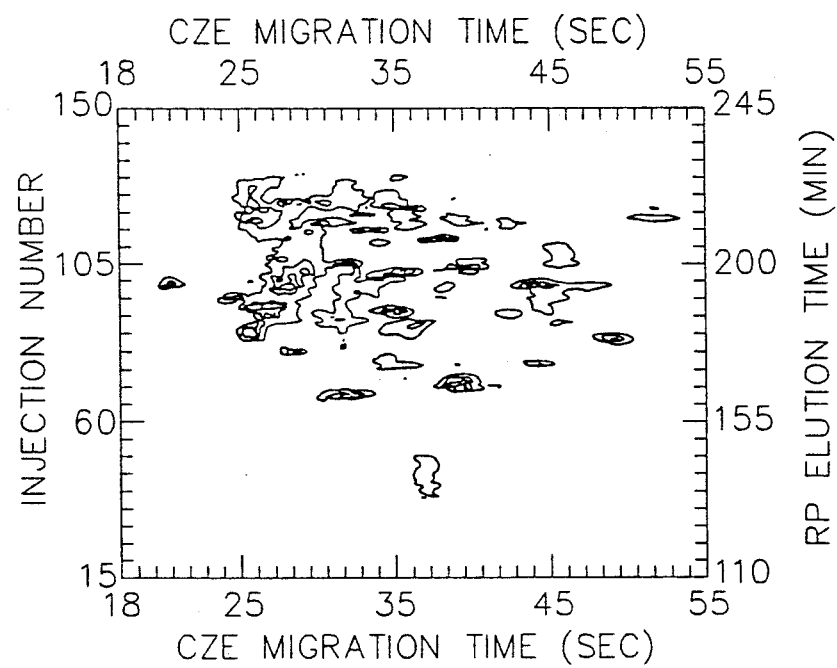
FIG. 7(b) shows a contour plot of the same data set. Tic marks on injection number axis represent 5 injections and 5 minutes each

FIG. 7a is a chromatoelectropherogram of the 2-D separation of the digest sample. One injection on the CZE system was made every minute. Each tic mark on the RP elution time axis represents 5 CZE injections. Injection numbers 15 through 150 are displayed. The gradient used on the LC column was identical to that used for obtaining the data for FIG. 6a. Well over 30 peaks can be counted in FIG. 7a, although not all are fully resolved. No attempt was made to identify any of these peaks. Because this sample is so complex it is difficult to visually distinguish all peaks with this type of data display, and other viewing angles simply obscure different peaks. A more useful type of data display for complex samples is shown in FIG. 7b. This is a contour map of FIG. 7a. Here the number of peaks is more easily established, and distinguishing one peak from another becomes easier.

Other display options are shown in FIG. 8. Each plot in this figure is obtained from the same data set displayed in FIG. 7. Summing together all points in each electropherogram, produces a simulation of the RP chromatogram of the total original sample shown in FIG. 8a. The final result of this process appears undersampled since the number of points is equal to the number of CZE injections, and some peaks may only appear in one or two CZE injections. The peak containing region of FIG. 8a appears to be more compressed than that in FIG. 6a, the actual first column separation of this sample. Because the first column is undersampled by the CZE system, this undersampling may severely distort the simulated chromatogram. This may account for the different profiles evident in FIGS. 8a and 6a. In FIG. 7a, the baseplane can be seen to drift slightly downward. This manifests itself in FIG. 8a as a large sloping baseline evident most noticeably at the beginning of the plot. Although the simulated method appears to be a poor approximation of the actual first column chromatogram, it may provide a method for roughly estimating system performance and reproducibility.

Figure 8A:
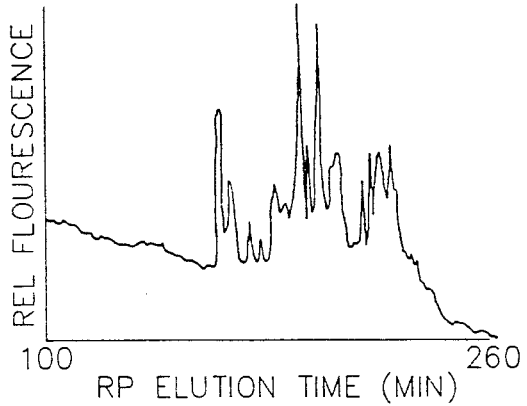
FIG. 8(a) shows a simulated chromatogram of total original sample produced by summation of electropherogram data points from injections 5 through 165. Data points from 18 to 55 seconds included.
Figure 8B:
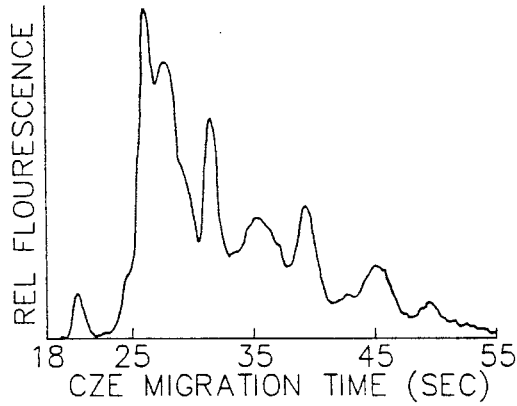
FIG. 8(b) shows a simulated electropherogram of total original sample produced by summation of chromatogram data points from injections 15 through 150. Data points from 18 to 55 seconds included.

FIG. 8b is a simulated electropherogram of the total original sample obtained by summing together corresponding points on each electropherogram, or put another way, summing all points together in each "chromatogram". The result shows good agreement with FIG. 6b, the actual electropherogram of the entire original sample. It should be noted that these two data sets were obtained on different days, as were the data sets compared in FIGS. 8a and 6a, and that may explain the slight differences in migration times for corresponding peaks.

Figure 8C:
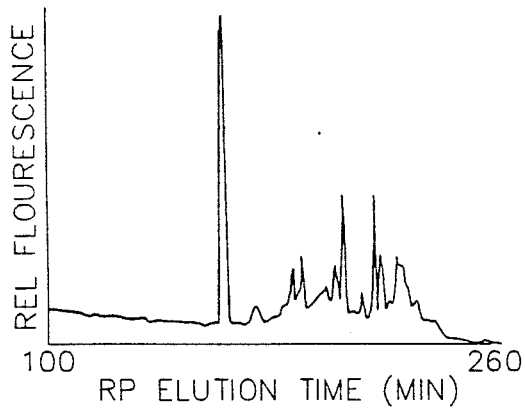
FIG. 8(c) shows a plot of simulated chromatogram for points between 30 and 35 seconds on the CZE migration time axis. Injections 5 through 165 included.
Figure 8D:
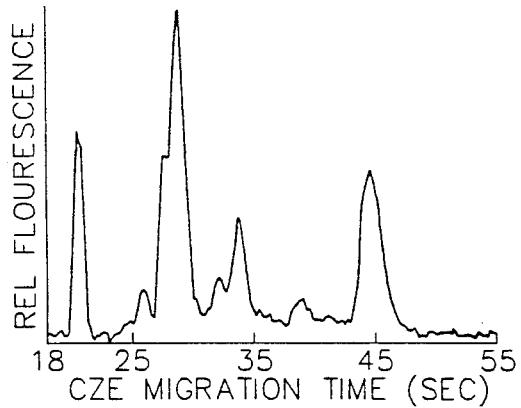
FIG. 8(d) shows a plot of single electropherogram occuring at 198 minutes on the RP elution time axis.

FIG. 8c is a chromatogram "slice" of the 3-D chromatoelectropherogram. The width of this slice contains all points in the range of 30 to 35 seconds on the electropherogram. The width of this "slice" may also be enlarged to cover a larger specific mobility range by summing together other "slices". It should be noted that this type of plot is only approximate. Very large peaks lying on the outer edge of the CZE summation range will prejudice the final plot in their favor. Small peaks lying totally within the desired mobility range may be poorly represented in the final plot. FIG. 8d is a plot of a single CZE injection from the chromatoelectropherogram in FIG. 7. Injection number 103, which contains the fastest migrating peak in the sample, is plotted.

DISCUSSION. Clearly RP HPLC and CZE are orthogonal separation methods. As such, their 2-D operation is effective, yet not trivial to achieve. The fact that they are orthogonal is demonstrated in FIG. 7b. The lack of a specific diagonal pattern of peaks shows these methods to be highly orthogonal. In addition, both methods are shown to be able to separate species the other cannot separate. As stated above, CZE has already been shown to be able to separate species that RP HLPC cannot, but the method presented here shows the opposite to be true also. While it may be expected that RP HPLC can separate co-migrating species at the electroosmotic flow migration time, examination of FIG. 7b shows RP HPLC to separate species that co-migrate at a variety of CZE migration times.

As stated earlier, the more orthogonal two separation mechanisms are, the more effective and the more difficult will be their coupling. One dissimilarity of these two techniques which must be considered is the use of increasing organic mobile phase in the RP HPLC portion of the system. Although anticipated as a CZE injection problem, we discovered no such problems when trying to inject samples on the CZE portion of the system from solutions with varying amounts of organic component. Another aspect to consider is that of analysis time. Most of the data presented here demanded over 4 hours of data acquisition time alone. While a large amount of information is obtained, shorter analysis times are always desirable. Greater resolution could be obtained on the RP column by use of a different gradient at the expense of a longer chromatographic elution time. However, as stated earlier, memory limits determine the longest amount of time during which the CZE system can operate with a sufficiently high data acquisition rate. CZE resolution could also be improved by increasing the useful capillary length. However, it is vitally important for the CZE injection system to sample the first column as frequently as possible. The shorter the CZE analysis time for each injected sample, the more frequent the CZE sampling rate. Even at 1 minute sampling times, we are undoubtedly undersampling the RP column.

Another aspect of incompatibility is that of system volumes. In general it would be desirable for effluent volumes of the first dimension to match the sample volumes of the second dimension, as was the case in our earlier work in LC—LC noted above. Such a situation provides for a more efficient use of sample. The microbore column used in this work produces far too much volume for the CZE system to sample entirely. Coupling an open tubular LC column or a packed capillary column with CZE would more closely match system volumes, but would be more technically difficult.

We believe this to be the first example of electromigration injection from a flowing stream. This technique warrants more investigation and characterization, and it has several interesting advantages. First, injections are performed at the grounded electrode and no capillary manipulations are necessary. This feature has obvious safety advantages but also has advantages for applications where capillary manipulation is either difficult or undesired. Another feature of this injection method is that it provides for a convenient method of producing gradients during the electrophoresis. Although not used in the application described here, gradients may be desired for CZE, or particularly for MECC applications. If pump 40 is replaced with a pump capable of creating a gradient, the electroosmotic flow will continuously pull this gradient in to the CZE capillary during the course of the analysis.

It should be noted that while specific migration times and elution times can change for a particular sample from day-to-day, the general appearance and relative intensities, at least to a first approximation, of the 3-D chromatoelectropherogram of different tagged samples of the same ovalbumin digest are similar. The contour type data display may provide a means of obtaining digest fingerprints of different proteins which would be more reliable than single dimension fingerprinting since three variables are obtained for each peak, migration time, elution time and relative intensity. Although specific migration/elution times can change, it should be possible based upon the general pattern, to determine if one sample is a different protein or if one sample has more or less peaks than another sample. Single amino acid changes in proteins would have a greater possibility of being detected with this 2-D method than reliance on single dimension fingerprints.

The foregoing is illustrative of the present invention, and not to be construed as limiting thereof. The invention is defined by the following claims, with equivalents of the claims to be included therein.

That which is claimed is:

1. A two dimensional separation system, comprising:
    a liquid chromatography column having an outlet port;
    an electrophoresis capillary having an inlet end and an outlet end;
    buffer supply means having an outlet end;
    a sample storage loop having an inlet end and an outlet end;
    a waste line having an inlet end;
    valve means connected to said capillary inlet end, said chromatography outlet port, said buffer supply means outlet end, said storage loop inlet end, said storage loop outlet end, and said waste line inlet end, said valve means switchable between a run configuration and an inject configuration;
    with said valve means in said run configuration simultaneously (a) conducting effluent from said chromatography column through said storage loop and to said waste line, and (b) conducting effluent from said buffer supply means directly to said capillary inlet end;
    and with said valve means in said inject configuration simultaneously (a) conducting effluent from said chromatography column directly to said waste line, and (b) conducting effluent from said buffer supply means through said storage loop and to said capillary, whereby a sample of effluent from said chromatography column in said storage loop is flushed into said capillary by said buffer supply means;
    control means operably associated with said valve means for switching said valve means between said run configuration and said inject configuration; and
    a power supply operably connected to both said capillary inlet end and said capillary outlet end configured to providing a potential therebetween so that said capillary inlet end serves as an anode, said capillary outlet end serves as a cathode, and charged molecules in said capillary are carried from said inlet end to said outlet end by electromigration, with said power supply operably associated with said control means;
    wherein said control means includes means for reducing the potential between said capillary inlet end and said capillary outlet end when said valve means is in said inject position by an amount sufficient to hinder the electromigration of charged molecules therein.

2. A two-dimensional separation system according to claim 1, wherein said control means reduces the potential between said anode and said cathode at a predetermined time prior to switching said valve means from said first configuration to said second configuration, wherein said predetermined time is at least equal to the slew time required to reduce the potential between said capillary inlet end and said capillary outlet end by an amount sufficient to hinder the electromigration of charged molecules therein.

3. A two-dimensional separation system according to claim 1, wherein said control means restores the potential between said capillary inlet end and said capillary outlet end when said valve means is switched from said second configuration to said first configuration.

4. A two-dimensional separation system according to claim 1, further comprising a detector operably associated with said capillary for detecting molecules in said capillary, with said control means operably associated with said detector for collecting data therefrom, and wherein said control means interrupts data collection from said detector upon reducing the potential between said capillary inlet end and said capillary outlet end.

5. A two-dimensional separation system according to claim 1, further comprising a waste line connected to said valve means, wherein said valve means in said first configuration conducts effluent from said chromatography column to said waste line.

6. A two-dimensional separation system according to claim 1, further comprising means for supplying a continuous stream of fluid solution to said liquid chromatography column.

7. A two dimensional separation system according to claim 11, said system further comprising:
    detecting means for detecting the quantities of components in said capillary;
    calculating means responsive to said detecting means for calculating the concentrations of individual components of said mixture from said quantity detection; and display means responsive to said calculating means for producing three dimensional plots illustrating the components of said of mixture, wherein a first axis of said plot illustrates the duration that components remain in said liquid chromatography column, a second axis of said plot illustrates the migrating distance of said components within said capillary and a third axis of said plot represents the concentration of said components.

8. A two dimensional separation system according to claim 7, wherein said calculating means comprises a stored program running on a general purpose computer.

9. A two dimensional separation system according to claim 7, wherein said detection means detects the fluorescence of said mixture components.

10. A two dimensional separation system according to claim 1, further comprising:
  detecting means for detecting the quantities of components in said capillary;
  calculating means responsive to said detecting means for calculating the concentrations of individual components of said mixture from said quantity detection; and
  display means responsive to said calculating means for producing a two dimensional graph, one axis of said graph illustrating either component duration in said chromatography column or duration in said capillary, and the other axis of said graph illustrating component concentration.

11. A two dimensional separation system according to claim 10, wherein said calculating means comprises a stored program running on a general purpose computer.

12. A two dimensional separation system according to claim 10, wherein said detection means detects fluorescence of said mixture components.

13. A subassembly useful in constructing a two-dimensional separation system which includes a first separation system having an outlet port, a second capillary electrophoresis separation system comprised of a capillary having an inlet end and an outlet end, a buffer supply means having an outlet end, and a power supply operably connected to both said capillary inlet end and said capillary outlet end and configured for providing a potential therebetween so that said inlet end serves as an anode, said outlet end serves as a cathode, and charged molecules in said capillary are carried from said inlet end to said outlet end by electromigration; said subassembly comprising:
  a storage control loop having an inlet end and an outlet end;
  valve means having a waste outlet, said valve means connected to said capillary inlet end, said first separation system outlet port, said storage loop inlet end, said storage loop outlet end, and said buffer supply means, said valve means switchable between a run configuration and an inject configuration; and
  control means operably associated with said valve means for switching said valve means between said run configuration and said inject configuration;
  with said valve means in said run configuration configured for simultaneously (a) conducting effluent from said first separation system through said storage loop and to said waste outlet, and (b) conducting effluent from said buffer supply means directly to said capillary inlet end;
  and with said valve means in said inject configuration configured for simultaneously (a) conducting effluent from said first separation system directly to said waste outlet, and (b) conducting effluent from said buffer supply means through said storage loop and to said capillary, whereby a sample of effluent from said chromatography column in said storage loop is flushed into said capillary by said buffer supply means;
  wherein said control means includes means for reducing the potential between said capillary inlet and said capillary outlet end when said valve means is in said inject position by an amount sufficient to hinder the electromigration of charged molecules therein.

14. A subassembly according to claim 13, wherein said control means includes means for reducing the potential between said anode and said cathode at a predetermined time prior to switching said valve means from said first configuration to said second configuration, wherein said predetermined time is at least equal to the slew time required to reduce the potential between said capillary inlet end and said capillary outlet end by an amount sufficient to hinder the electromigration of charged molecules therein.

15. A subassembly according to claim 13, wherein said control means includes means for restoring the potential between said capillary inlet end and said capillary outlet end when said valve means is switched from said second configuration to said first configuration.

16. A subassembly according to claim 13, wherein said two dimensional separation system further includes a detector operably associated with said capillary for detecting molecules in said capillary, wherein said control means includes means for interrupting data collection from said detector upon reducing the potential between said capillary inlet end and said capillary outlet end.

* * * * *

UNITED STATES PATENT AND TRADEMARK OFFICE
CERTIFICATE OF CORRECTION

PATENT NO. : 5,131,998

DATED : 21 July 1992

INVENTOR(S) : James W. Jorgenson, Michelle M. Bushey

It is certified that error appears in the above-identified patent and that said Letters Patent is hereby corrected as shown below:

Column 5, line 22, please delete "15".

Column 6, line 29, please change "5 µL" to --52 µL--.

Column 6, line 39, please change "250 mm X 1.0" to
--250 mm X 1.0 mm,--.

Column 11, line 12, please change "separation" to
--Separation--.

Column 16, line 62, Claim 7, please change "claim 11" to
--claim 1--.

Signed and Sealed this

Twenty-first Day of September, 1993

Attest:

BRUCE LEHMAN

*Attesting Officer*     *Commissioner of Patents and Trademarks*